Figure 3:
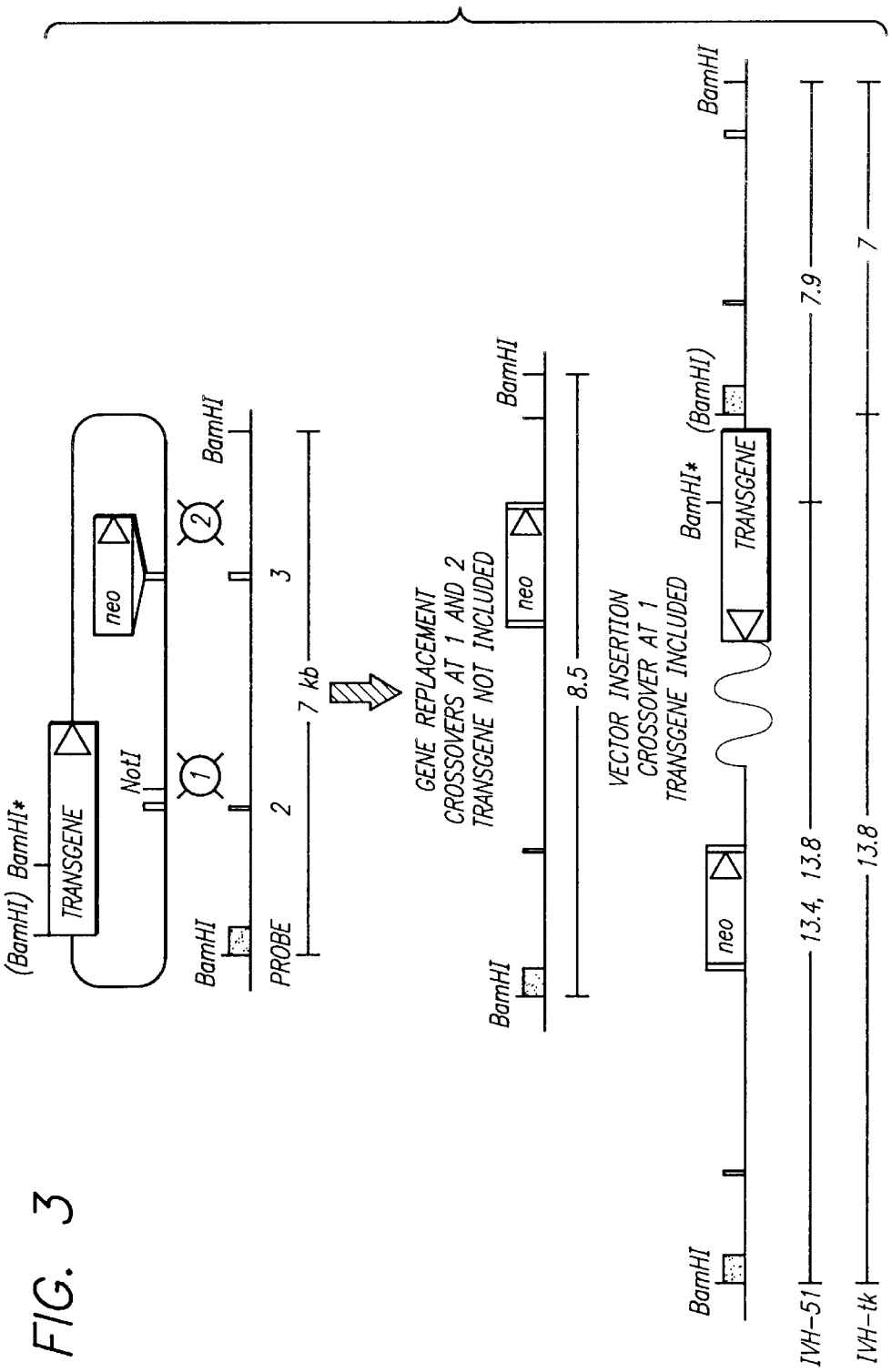

United States Patent [19]
Hasty

[11] Patent Number: 6,037,125
[45] Date of Patent: *Mar. 14, 2000

[54] DISRUPTION OF THE MAMMALIAN RAD51 PROTEIN AND DISRUPTION OF PROTEINS THAT ASSOCIATE WITH MAMMALIAN RAD51 FOR HINDERING CELL PROLIFERATION AND/OR VIABILITY OF PROLIFERATING CELLS

[75] Inventor: Paul Hasty, Magnolia, Tex.

[73] Assignee: Lexicon Genetics Incorporated, The Woodlands, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/758,280

[22] Filed: Nov. 5, 1996

[51] Int. Cl.$^7$ .................................................... C12Q 1/68
[52] U.S. Cl. ..................................................................... 435/6
[58] Field of Search .............................. 435/6, 172.3, 441

[56] References Cited

PUBLICATIONS

Shen et al., *J. Biol. Chem.*, vol. 271, 1996, pp. 148–152.
Aboussekhra et al., 1992, "Semidominant Suppressors of Srs2 Helicase Mutations of *Saccharomyces cerevisiae* Map in the RAD51 Gene, Whose Sequence Predicts a Protein with Similarities to Procaryotic RecA Proteins," *Mol. Cell. Biol.* 12:3224–3234.
Ashley et al., 1995, "Dynamic changes in Rad51 distribution on chromatin during meiosis in male and female vertebrates," *Chromosoma* 104:19–28.
Baker et al., 1990, "Suppression of Human Colorectal Carcinoma Cell Growth by Wild–Type p53," *Science* 249:912–915.
Basile et al., 1992, "Nucleotide Sequence and Transcriptional Regulation of the Yeast Recombinational Repair Gene RAD51," *Mol. Cell. Biol.* 12:3235–3246.
Bendixen et al., 1994, "Identification of a Mouse Homologue of the *Saccharomyces cerevisiae* Recombination and Repair Gene, RAD52," *Genomics* 23:300–303.
Bennett et al., 1993, "Lethality induced by a single site–specific double–strand break in a dispensable yeast plasmid," *Proc. Natl. Acad. Sci. U.S.A.* 90:5613–5617.
Benson et al., 1994, "Purification and characterization of the human Rad51 protein, an analogue of *E. coli* RecA," *EMBO Journal* 13:5764–5771.
Bezzubova et al., 1993, "A chicken RAD51 homologue is expressed at high levels in lymphoid and reproductive organs," *Nucleic Acids Res.* 21:1577–1580.
Bishop, 1994, "RecA Homologs Dmc1 and RAD51 Interact to Form Multiple Nuclear Complexes Prior to Meiotic Chromosome Synapsis," *Cell* 79:1081–1092.
Bradley et al., 1992, "Modifying the Mouse: Design and Desire," *Bio/Technology* 10:534–539.
Carr and Hoekstra, 1995, "The cellular responses to DNA damage," *Trends in Cell Biology* 5:32–40.
Cleaver, 1994, "It Was Very Good Year for DNA Repair," *Cell* 76:1–4.

Derossi et al., 1994, "The Third Helix of the Antennapedia Homeodomain Translocates through Biological Membranes," *J. Biol. Chem.* 269:10444–10450.
Donehower et al., 1992, "Mice deficient for p53 are developmentally normal but susceptible to spontaneous tumours," *Nature* 356:215–221.
Donovan et al., 1994, "Homotypic and heterotypic protein associations control Rad51 function in double–strand break repair," *Genes and Develop.* 8:2552–2562.
Haaf et al., 1995, "Nuclear foci of mammalian Rad51 recombination protein in somatic cells after DNA damage and its localization in symanptonemal complexes," *Proc. Natl. Sci. U.S.A.* 92:2298–2302.
Habu et al., 1996, "The mouse and human homologs of DMC1, the yeast meiosis–specific homologous recombination gene, have a common unique form of exon–skipped transcript in meiosis," *Nucleic Acids Res.* 24:470–477.
Harvey et al., 1993, "In vitro growth characteristics of embryo fibroblasts isolated from p53–deficient mice," *Oncogene* 8:2457–2467.
Hays et al., 1995, "Complex formation in yeast double–strand break repair: Participation of Rad51, Rad52, Rad55 and Rad57 proteins," *Proc. Natl. Acad. Sci. U.S.A.* 92:6925–6929.
Horii et al., 1992, "Inhibitory Effects of N– and C–terminal Truncated *Escherichia coli* recA Gene Products on Functions of the Wild–type recA Gene," *J. Mol. Biol.* 223:105–114.
Inouye et al., 1994, "Isolation of cDNA Encoding a Metal Response Element Binding Protein Using a Novel Expression Cloning Procedure: The One Hybrid System," *DNA Cell. Biol.* 13(7):731–742.
Jang et al., 1994, "Cloning and sequencce analysis of rhp51$^+$, a *Schizosaccharomyces pombe* homolog of the *Saccharomyces cerevisiae* RAD51 gene," *Gene* 142:207–211.
Jeggo, 1990, "Studies on mammalian mutants defective in rejoining double–strand breaks in DNA," *Mutation Research* 239:1–16.

(List continued on next page.)

*Primary Examiner*—James Ketter
*Attorney, Agent, or Firm*—Pennie & Edmonds LLP

[57] ABSTRACT

When a mutation, designated rad51$^{M1}$, was generated in the mouse MmRAD51 gene, mutant embryos died shortly after implantation. rad51$^{M1}$ cells exhibited hypersensitivity to ionizing radiation, reduced proliferation, programmed cell death and chromosome loss. The disruption of MmRad51 rotein-protein interactions stopped cell proliferation and/or reduced cell viability. Several proteins that interact with MmRad51 have been identified including, for example Brca2 and M96. Additionally, Rad51 self-associates via the N-terminal region. When a single residue was changed from a conserved lysine to an alanine, the alteration proved toxic to cells. Moreover, a rad51 allele that lacked the RecA homology region was also deleterious to cells. In view of the above, it is clear that inhibiting MmRad51 function or the function of any molecule that associates with MmRad51, or any molecule in the Rad51 or Rad52 pathways, hinders cell proliferation and/or viability. Accordingly, molecules capable of blocking these critical DNA repair pathways may be effective as therapeutics for inhibiting cell proliferation.

15 Claims, 2 Drawing Sheets

OTHER PUBLICATIONS

Johnson and Symington, 1995, "Functional Differences and Interactions among the Putative RecA Homologs Rad51, Rad55, and Rad57," *Mol. Cell. Biol.* 15:4843–4850.

Kastan et al., 1991, "Participation of p53 Protein in the Cellular Response to DNA Damage," *Cancer Research* 51:6304–6311.

Kirchgessner et al., 1995, "DNA–Dependent Kinase (p350) as a Candidate Gene for the Murine SCID Defect," *Science* 267:1178–1183.

Ko and Prives, 1996, "p53: puzzle and paradigm," *Genes and Develop.* 10:1054–1072.

Krasin and Hutchinson, 1977, "Repair of DNA Double–strand Breaks in *Escherichia coli*, which Requires recA Function and the Presence of a Duplicate Genome," *J. Mol. Biol.* 116:81–98.

Kuerbitz et al., 1992, "Wild–type p53 is a cell cycle checkpoint determinant following irradiation," *Proc. Natl. Acad. Sci. U.S.A.* 89:7491–7495.

Liang et al., 1996, "Chromosomal double–strand break repair in Ku80–deficient cells," *Proc. Natl. Acad. Sci. U.S.A.* 93:8929–8933.

Lim and Hasty, 1996, "A mutation in mouse rad51 results in an early embryonic lethal that is suppressed by a mutation in p53," *Mol. Cell. Biol.* 16(12):7133–7143.

Lowe et al., 1994, "p53 Status and the Efficacy of Cancer Therapy in Vivo," *Science* 266:807–810.

Lu and Lane, 1993, "Differential Induction of Transcriptionally Acive p53 Following UV or Ionizing Radiation: Defects in Chromosome Instability Syndromes?" *Cell* 75:765–778.

Malkova et al., 1996, "Double–strand break repair in the absence of RAD51 i yeast: A possible role for break–induced DNA replication," *Proc. Natl. Acad. Sci. U.S.A.* 93:7131–7136.

Milne and Weaver, 1993, "Dominant negative alleles of RAD52 reveal a DNA repair/recombination complex including Rad51 and Rad52," *Genes and Develop.* 7:1755–1765.

Morita et al., 1993, "A mouse homolog of the *Escherichia coli* recA and *Saccharomyces cerevisiae* RAD51 genes," *Proc. Natl. Acad. Sci. U.S.A.* 90:6577–6580.

Mortimer, 1958, "Radiobiological and Genetic Studies on a Polyploid Series (Haploid to Hexaploid) of *Saccharomyces cerevisiae*," *Radiat. Res.* 9:312–326.

Muris et al., 1993, "Cloning the RAD51 homologue of *Schizosaccharomyces pombe*," *Nucleic Acids Res.* 21:4586–4591.

Norioka et al., 1995, "Two recA Genes in *Myxococcus xanthus*," *J. Bacteriol.* 177:4179–4182.

Nussenzweig et al., 1996, "Requirement for Ku80 in growth and immunoglobulin V(D)J recombination," *Nature* 382:551–555.

Park et al., 1996, "Physical Interaction between human Rad52 and RPA Is Required for Homologous Recombination in Mammalian Cells," *J. Biol. Chem.* 1996:18996–19000.

Resnick et al., 1989, "Lack of DNA homology in a pair of divergent chromosomes greatly sensitizes them to loss by DNA damage," *Proc. Natl. Acad. Sci. U.S.A.* 86:2276–2280.

Rockmill et al., 1995, "Roles for two RecA homologs in promoting meiotic chromosome synapsis," *Genes and Develop.* 9:2684–2695.

Schiestl et al., 1989, "Cloning and Sequence Analysis of the *Saccharomyces cerevisiae* RAD9 Gene and Further Evidence that Its Product is Required for Cell Cycle Arrest Induced by DNA Damage," *Mol. Cell. Biol.* 9:1882–1896.

Schlissel et al., 1993, "Double–strand signal sequence breaks in V(D)J recombination are blunt, 5'–phosphorylated, RAG–dependent, and cell cycle regulated," *Genes and Develop.* 7:2520–2532.

Shen et al., 1995, "The Human and Mouse Homologs of the Yeast RAD52 Gene: cDNA Cloning, Sequence Analysis, Assignment to Human Chromosome 12p12.2–p13, and mRNA Expression in Mouse Tissues," *Genomics* 25:199–206.

Shen et al., 1996, "Specific Interactions between the Human RAD51 and RAD52 Proteins," *J. Biol. Chem.* 271:148–152.

Shinohara et al., 1992, "Rad51 Protein Involved in Repair and Recombination in *S. cerevisiae* Is a RecA–like Protein," *Cell* 69:457–470.

Shinohara et al., 1993, "Cloning of human, mouse and fission yeast recombination genes homologous to RAD51 and recA," *Nature Genet.* 4:239–43.

Story et al., 1992, "The structure of the *E. coli* recA protein monomer and polymer," *Nature* 355:318–325.

Story et al., 1993, "Structural Relationship of Bacterial RecA Proteins to Recombination Proteins from Bacteriophage T4 and Yeast," *Science* 259:1892–1896.

Sugawara et al., 1995, "DNA structure–dependent requirements for yeast RAD genes in gene conversion," *Nature* 373:84–86.

Sung, 1994, "Catalysis of ATP–Dependent Homologous DNA Pairing and Strand Exchange by Yeast RAD51 Protein," *Science* 265:1241–1243.

Sung and Robberson, 1995, "DNA Strand Exchange Mediated by a RAD51–ssDNA Nucleoprotein Filament with Polarity Opposite to That of RecA," *Cell* 82:453–461.

Symonds et al., 1994, "p53–Dependent Apoptosis Suppresses Tumor Growth and Progression In Vivo," *Cell* 78:703–711.

Tateishi et al., 1992, "C–terminal Truncated *Escherichia coli* RecA Protein RecA5327 Has Enhanced Binding Affinities to Single– and Double–Stranded DNAs," *J. Mol. Biol.* 223:115–129.

Tavtigian et al., 1996, "The complete BRCA2 gene and muations in chromosome 13q–linked kindreds," *Nature Gen.* 12:333–337.

Terasawa et al., 1995, "Localization of RecA–like recombination proteins on chromosomes of the lily at various meiotic stages," *Genes and Develop.* 9:925–934.

Tsuzuki et al., 1996, "Targeted disruption of the Rad51 gene leads to lethality in embryonic mice," *Proc. Natl. Acad. Sci. U.S.A.* 93:6236–6240.

Vogelstein, 1990, "A deadly inheritance," *Nature* 348:681–682.

Weinert and Hartwell, 1988, "The RAD9 Gene Controls the Cell Cycle Response to DNA Damage in *Saccharomyces cerevisiae*," *Science* 241:317–322.

Wooster et al., 1995, "Identification of the breast cancer susceptibility gene BRCA2," *Nature* 378:789–792.

Yamamoto et al., 1996, "Cell cycle–dependent expression of the mouse Rad51 gene in proliferating cells," *Mol. Gen. Genet.* 251:1–12.

Yoshimura et al., 1993, "Cloning and sequence of the human RecA–like gene cDNA," *Nucleic Acids Res.* 21:1665.

Zhu et al., 1996, "Ku86–Deficient Mice Exhibit Severe Combined Immunodeficiency and Defective Processing of V(D)J Recombination Intermediates," *Cell* 86:379–389.

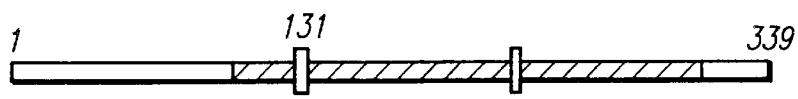
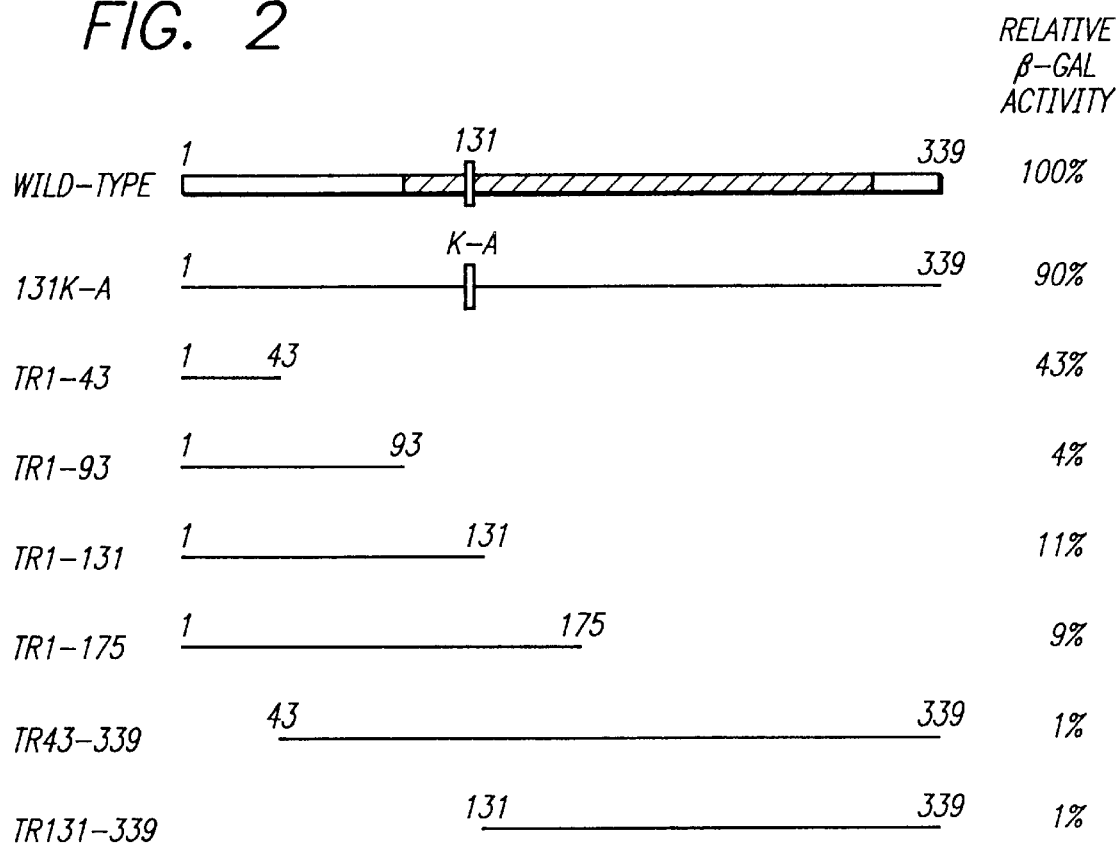

DISRUPTION OF THE MAMMALIAN RAD51 PROTEIN AND DISRUPTION OF PROTEINS THAT ASSOCIATE WITH MAMMALIAN RAD51 FOR HINDERING CELL PROLIFERATION AND/OR VIABILITY OF PROLIFERATING CELLS

1.0. FIELD OF THE INVENTION

The present invention relates to molecules that disrupt mammalian Rad51 or Rad52 function, or disrupt the function of other molecules that are involved in the Rad51 or Rad52 pathways. Such molecules are useful as a means to hinder cell proliferation or to promote programmed cell death, and define a novel class of therapeutic agents for use in the treatment of proliferative disorders such as autoimmune disease and cancer.

2.0. BACKGROUND OF THE INVENTION

DNA repair and recombination are required by organisms to prevent the accumulation of mutations and to maintain the integrity of genetic information. Damaged genetic material may result in cell cycle arrest, programmed cell death, chromosome loss or cell senescence. Alternatively, compromised genetic information may result in dysregulation of the cell cycle ultimately leading to increased cellular growth and tumor formation.

The repair of double-strand breaks (DSB) in DNA is an essential cellular process. DSB repair may occur during general cellular functions such as DNA repair (Friedberg et al., 1995, DNA Repair and Mutagenesis. American Society for Microbiology, Washington, D.C.). In bacteria and yeast cells, DSB are predominately repaired by a homologous recombination pathway (Krasin and Hutchinson, 1977, J. Mol. Biol. 116:81–98; Mortimer, 1958, Radiat. Res. 9:312–16. In the budding yeast $Saccharomyces\ cerevisiae$ the RAD52 epistasis group (Rad50 to Rad57, Mre11 and Xrs2) was identified in cells sensitive to ionizing radiation (reviewed in Friedberg, 1995; Petes et al., 1991, Recombination in yeast., p. 407–521. In J. R. P. J. R. Broach, and E. W. Jones (ed.), The Molecular and Cellular Biology of the Yeast Saccharomyces. Cold Spring Harbor Laboratory Press, Cold Spring Harbor, N.Y.). Later, some of the members of this group were shown to be important for recombinational repair (e.g., Rad51, Rad52, Rad54, Rad55, Rad57 (Malkova et al., 1996, Proc. Natl. Acad. Sci. USA 93:7131–36, Sugawara et al., 1995, Nature 373:84–86).

Among the members of the RAD52 epistasis group, ScRad51 is particularly interesting because it shares similarity with the $Escherichia\ coli$ recombination protein, RecA. ScRad51 and RecA polymerize on double-stranded and single-stranded DNA (dsDNA, ssDNA) to produce a helical filament, and both enzymes catalyze an ATP-dependent strand exchange between homologous DNA molecules (Ogawa et al., 1993, Science 259:1896–99; Sung, 1994, Science 265:1241–4364; Sung and Robberson, 1995, Cell 82:453–61). ScRad51 and RecA share 30% homology over a span of about 220 amino acids, and each protein contains two conserved ATP binding motifs (Aboussekhra et al., 1992, Mol. and Cell. Biol. 12:3224–34; Basile et al., 1992, Mol. Cell. Biol. 12:3235–46; Sugawara et al., 1995, Nature 373:84–86).

ScRad51 repairs DSB by homologous recombination. DSB accumulate at recombination hot spots during meiosis in cells that lack ScRad51 (Sugawara, 1995), and ScRad51 localizes to meiotic nuclei (Bishop, 1994, Cell 79:1081–92) and promotes meiotic chromosome synapsis (Rockmill et al., 1995, Genes & Develop. 9:2684–95). Accordingly, it is thought that ScRad51 mediates meiotic recombination by binding to single-strands generated at DSB which are in strand pairing and exchange during meiosis (Sung and Robberson, 1995, Cell 82:453–61).

A variety of direct and indirect protein-protein interactions are essential for RecA and ScRad51 function. The crystal structure of RecA suggests that a portion of the N-terminal region is involved in polymer formation (Story et al., 1993, Science 259:1892–96; Story et al., 1992, Nature 355:318–324) which was supported by genetic analysis that showed C-terminal truncations dominantly interfered with DNA repair in wild-type bacteria (Horii et al., 1992, J. Mol. Biol. 223:104–114; Tateishi et al., 1992, J. Mol. Biol. 223:115–129; Yarranton et al., 1982, Mol. Gen. Genet. 185:99–104). A similar self-association region occurs in the N-terminal region of ScRad51 and is essential for DNA repair (Donovan et al., 1994, Genes & Develop. 8:2552–2562; Shinohara et al., 1992, Cell 69:457–70). ScRad51 also associates with Rad52 and Rad55 (Hays et al., 1995, Proc. Natl. Acad. Sci USA 92:6925–6929; Johnson and Symington, 1995, Molec. Cell. Biol. 15(9):4843–4850; Milne and Weaver, 1993, Genes & Develop. 7:1755–1765) as well as other proteins. Other protein interactions may be inferred because a rad51Δ rad52Δ strain of $S.\ cerevisiae$ was only partially complemented by Rad51 and Rad52 from $Kluyveromyces\ lactis$ (Donovan et al., 1994, Genes & Develop. 8:2552–2562), and because ScRad51 colocalized with Dmc1 to the synaptonemal complex (Bishop, 1994, Cell 79:1081–92). These data suggest that a large protein complex is necessary for recombinational repair and that disruption of any of the proteins in this complex hinders the repair of DSB.

RecA/ScRad51 homologues have been discovered in a wide range of organisms including the fission yeast $Schizosaccharomyces\ pombe$ (Jang et al., 1994, Gene 142:207–11; Muris et al., 1993, Nuc. Acids Res. 21:4586–91; Shinohara et al., 1993, Nature Genet. 4:239–4358), lilies (Terasawa et al., 1995, Genes & Develop. 9:925–34), chickens (Bezzubova et al., 1993, Nucl. Acids Res. 21:1577–80), mice (Morita et al., 1993, Proc. Natl. Acad. Sci USA 90:6577–80; Shinohara et al. 1993, Nature Genet. 4:239–43) and humans (Shinohara et al. 1993; Yoshimura et al., 1993, Nucl. Acids Res. 21:1665), and appear to be involved in DNA repair and recombination based on the following evidence: 1) Conserved RecA homology—MmRad51 is 83% homologous, 69% identical to ScRad51, and 51% homologous, 28% identical to RecA. Shared homology between mammalian and yeast Rad51 suggest conserved function due to the remarkable similarity between other mammalian and yeast DNA repair pathways (reviewed in Cleaver, 1994, Cell 76:1–4); 2) Expression pattern—MmRAD51 is highly expressed in tissues involved in meiotic recombination such as testes (Morita et al., 1993, Proc. Natl. Acad. Sci USA 90:6577–80) and ovaries (Shinohara et al., 1993, Nature Genet. 4:239–43). Additionally, expression of the $S.\ pombe$ MmRad51 homologue SpRAD51 increased after cells were treated with methyl methanesulfonate which provides further evidence of a DNA repair function (Jang et al., 1994, Gene 142:207–11); 3) Protein cellular localization—Mouse, chicken, and lily Rad51 localizes at discrete foci on meiotic chromosomes at varying concentrations during prophase 1, possibly on the lateral elements and recombination nodules, which suggests a role in the repair of DSB during meiotic recombination (Ashley et al., 1995, Chromosoma 104:19–28; Haaf et al., 1995, Proc. Natl. Acad. Sci. USA 92:2298–2302; Terasawa et al., 1995). Moreover, increasing concentrations of human Rad51, HsRad51, localize to the nucleus after exposure to DNA damaging agents which also suggests a repair function (Terasawa et al., 1995); 4) Filament formation on DNA—HsRad51 bind to ssDNA which demonstrates a potential for strand exchange (Benson et al., 1994, EMBO 13:5764–71); 5) Mouse cells with a rad51 mutation, designated rad.51$^{M1}$, displayed features that are known to be characteristic of unrepaired DSB in yeast cells (Lim and Hasty, 1996, In press) which include reduced proliferation, hypersensitivity to γ-radiation, chromosome loss and programmed cell death.

The function of MmRad51 is not completely understood; however, it is thought that, like ScRad51, it has, inter alia, a recombinational repair function. The recombinational repair pathway appears to be at least partially conserved between yeast and mammals. Mammalian homologues have been found for the members of the yeast Rad52 epistasis group (Rad51, Rad52), and to other yeast proteins (Dmc1) implicated in recombinational repair (Bendixen et al., 1994, Genomics 23:300–3035, Habu et al. 1996, Nucleic Acids Res. 24:470–7719; Morita et al., 1993, Proc. Natl. Acad. Sci USA 90:6577–80; Shen et al., 1995, Genomics 25:199–206; Shinchara et al., 1993). Expression pattern analysis supported the hypothesis that these homologues performed the same functions in yeast and mammals. MmRAD51 was highly expressed in tissues with cells involved in meiotic recombination, testis and ovary, and rapid cell division, intestine, embryo, and thymus (Morita et al., 1993; Shinohara et al., 1993). A role during meiotic recombination was further suggested because MmRAD51 was highly enriched in the synaptonemal complex in pachytene spermatocytes (Ashley et al., 1995; Haaf et al., 1995).

The most compelling evidence that MmRad51 and ScRad51 function is conserved comes from analysis of rad51 mutant cells, the mutation was designated rad51$^{M1}$ (Lim and Hasty, 1996).

3.0. SUMMARY OF THE INVENTION

An object of the present invention is to hinder cell proliferation or reduce cell viability by disrupting mammalian Rad51 function.

An additional object is to hinder cell proliferation or reduce cell viability by disrupting mammalian Rad52 function.

Another object of the present invention is to hinder cell proliferation or reduce cell viability by disrupting proteins that associate with mammalian Rad51.

Another object of the present invention is to hinder cell proliferation or reduce cell viability by disrupting proteins that associate with mammalian Rad52.

Another object of the present invention is to hinder cell proliferation or reduce cell viability by disrupting any proteins involved in the mammalian Rad51 or mammalian Rad52 pathways.

Another object of the present invention is to hinder cell proliferation or reduce cell viability by disrupting mammalian Rad51 protein interactions.

Another object of the present invention is to hinder cell proliferation or reduce cell viability by disrupting mammalian Rad52 protein interactions.

Another object of the present invention is to hinder cell proliferation or reduce cell viability by disrupting protein-protein interactions that are involved in the mammalian Rad51 or mammalian Rad52 pathways.

Yet another embodiment of the present invention involves methods of identifying compounds that are capable of inhibiting the binding or function of any protein involved in the Rad51 pathway, and, in particular, compounds capable of binding or inhibiting the function of Rad51 protein. Accordingly, an additional embodiment of the present invention involves methods of screening for compounds that disrupt double-stranded break repair by assaying for microsatellite formation in cells; assaying for chromosome loss in cells; assaying for the disruption of strand exchange in an in vitro assay; assaying for decreased cell proliferation; assaying for premature replicative cellular senescence; and assaying for increased cell death.

4.0. BRIEF DESCRIPTION OF THE DRAWINGS

FIG. 1. mRNA structure of MmRAD51. The predicted amino acids are numbered according to Shinohara et al., 1993. The shaded box represents the recA homology region. The open boxes represent regions that are not conserved across species. The thick vertical lines represent the ATP binding domains.

FIG. 2. MmRad51 self-association as demonstrated by the yeast two-hybrid system. The self-association is restricted to the most N-terminal 43 amino acids. The shaded box is the RecA core homology region (Shinohara et al, 1993). The thick vertical lines represent the ATP-binding sites. The open boxes represent regions that are not conserved between species. The relative β-galactosidase (β-gal) activities are presented, right panel. Full length wild-type MmRad51 is considered to be 100%. E12 served as a negative control and had 1% relative activity.

FIG. 3. Targeting the transgenes to the hprt locus. The hprt sequences contain exons 2 and 3 (labeled boxes). Hprt homology of vector origin is a thick line, of chromosomal origin is a thin line. The bacterial plasmid is represented by a wavy line. Potential locations for crossovers are X's labeled 1 or 2. Two recombination events are possible: either gene replacement with crossovers at both 1 and 2 or vector insertion with crossovers at either 1 or 2. For vector insertion, only a crossover at 1 is shown.

4.0. DETAILED DESCRIPTION OF THE INVENTION

As discussed above, one embodiment of the present invention is the expression of altered mammalian rad51 alleles that disrupt mammalian Rad51 function, mammalian Rad52 function, or the function of any other protein in the mammalian Rad51 or Rad52 pathways. Although the presently described invention has been specifically exemplified using a species exemplary of the order mammalia, given the relatively high level of interspecies sequence similarity (and functional similarity) observed in the Rad51 proteins, it is clear that the present invention may be broadly applied to other mammalian species, including humans, as well as nonmammalian animals such as birds, and fish.

In addition to mice, examples of mammalian species that may be used in the practice of the present invention include, but are not limited to: humans, non-human primates (such as chimpanzees), pigs, rats (or other rodents), rabbits, cattle, goats, sheep, and guinea pigs.

Reduced proliferation, hypersensitivity to γ-radiation, chromosome loss, and cell death have all been associated with rad51$^{M1}$ cells. These characteristics are similar to those seen in yeast cells deficient for recombinational repair either due to sequence divergence, or due to a mutation in rad51 or rad52 (Malkova et al., 1996, Proc. Natl. Acad. Sci. USA 93:7131–36; Resnick et al., 1989, Proc. Natl. Acad. Sci. USA 86:2276–80; Tsuzuki et al., 1996, Proc. Natl. Acad. Sci USA 93:6236–40). Even though these data suggest MmRad51 functions during recombinational repair it is also possible that the severe phenotype observed in rad51$^{M1}$ cells was due to disruption of another process.

For the purposes of the present application the term ionizing radiation shall mean all forms of radiation, including but not limited to $\alpha$, $\beta$, and $\gamma$ radiation and U.V. light, which are capable of directly or indirectly damaging the genetic material of a cell or virus. The term irradiation shall mean the exposure of a sample of interest to ionizing radiation, and the term radiosensitive shall refer to cells or individuals which display unusually adverse consequences after receiving moderate, or medically acceptable (i.e., non-lethal diagnostic or therapeutic doses), exposure to ionizing irradiation.

There is evidence that RecA homologues perform multiple functions, and that all functions are not performed by every homolog. For instance, of the two RecA homologues found in *Myxococcus xanthus*, only one is essential; however, both complement UV sensitivity in an *E. coli* recA strain (Norioka et al., 1995, J. Bacteriol. 177:4179–82). Also, two RecA homologues found in yeast, ScRad51 and Dmc1, are essential for meiotic recombination, but only ScRad51 is essential for mitotic recombination (Bishop, 1994, Rockmill et al. 1995, Genes & Develop. 9:2684–95). In mammals, a Dmc1 homologue has been isolated which suggests that, like yeast, mammalian RecA homologues also perform diverse and unique functions in mammalian cells (Habu et al., 1996).

MmRad51 may perform a novel role in DNA replication, repair, or chromosomal disjunction. MmRAD51 expression is restricted during the cell cycle to late $G_1/S/G_2$ and MmRAD51 expression was activated by mitogens that induced T and B cell proliferation suggesting a role in replication and repair (Yamamoto et al., 1996, 251:1–12). MmRad51 may take part in disjunction because it localizes to the kinetochores of diakinesis, and metaphase 1 chromosomes (Ashley et al., 1995).

The exact function or functions performed by MmRad51 are unimportant with regard to developing anti-proliferative drugs and cancer therapeutics as long as the disruption of the MmRad51 function provides a benefit to the patient. For the purposes of the present invention, it is assumed that the function of Rad51 is the repair of DSB; however, it is likely that Rad51 performs additional functions in the cell. However, it is important to note that at least some aspect of MmRad51 function is essential for cell proliferation and/or viability, and that molecules capable of disrupting MmRad51 function thus hinder cell proliferation or reduce cell viability. As such, any molecule that disrupts the MmRad51 pathway should prove useful for cancer therapy (for example). Furthermore, disruption of any protein-protein interaction that involves either MmRad51 or any other molecule in the MmRad51 pathway should also prove useful for cancer therapy.

Protein-protein interactions are critical for recombinational repair in yeast cells, including interactions that involve ScRad51 and ScRad52 (Donovan et al., 1994; Milne et al., 1993). In addition, the human Rad51 and Rad52 proteins were shown to associate like their yeast homologues (Shen et al., 1996, J. Biol. Chem. 271:148–152).

To isolate proteins that associate with MmRad51, a yeast two-hybrid screen was performed with MmRad51 as the "bait" and a T cell library and an embryonic cell library as the "prey". Among other proteins identified using this screen, MmRad51 and Brca2 were isolated, and the interactions identified using this screen may prove critical for in vivo function. Additional biochemical binding assays that may prove useful for identifying compounds that are able to associate with MmRad51 (or any other target protein) are well known in the art including, but not limited to: equilibrium or membrane flow dialysis, antibody binding assays, gel-shift assays, in vitro binding assays, filter binding assays, enzyme-linked immunoabsorbent assays (ELISA), western blots, co-immunoprecipitation, immunogold co-immunoprecipitation, coimmunolocalization, co-crystallization, fluorescence energy transfer, competition binding assays, chemical crosslinking, and affinity purification. In addition, genetic analysis may be used to identify accessory proteins that interact with MmRad51 or are peripherally involved in MmRad51 function. Where the MmRad51 accessory protein is essential to MmRad51 function, mutation in the genes encoding these proteins should typically result in phenotypes similar to those associated with MmRad51 mutations. Similarly, where the MmRad51 accessory proteins function to inhibit or retard MmRad51 activity, mutations in the genes encoding these factors shall generally mimic antagonist phenotypes.

The MmRad51 self-association was investigated further. Deletion analysis revealed that the MmRad51 self-association occurred in the N-terminal region which further demonstrated conservation of function with ScRad51 and RecA since both were shown to self-associate via the N-terminal region of the protein (Donovan et al., 1994; Horii, 1992; Story et al., 1992, 1993; Tateishi et al., 1992; Yarranton and Sedgwick, 1982).

Given the critical importance of mammalian Rad51 function, any disruption of the mammalian Rad51 or Rad52 complexes, or any member in their pathway will necessarily hinder cell proliferation or viability. When the Rad51 and Rad52 pathways were disrupted by introducing altered mouse rad51 into mouse cells, nonproductive protein-protein associations resulted. The altered forms of mouse rad51 were generated by disrupting a conserved nucleotide binding motif while preserving the protein association domain. The expression of these transgenes resulted in cellular toxicity. Presumably, the resulting nonproductive protein associations were responsible for the drastically reduced viability of these cells. In view of this result, it is clear one may reduce cell proliferation by disrupting mammalian Rad51 function, or the function of any protein in this repair pathway by hindering protein association by using defective proteins or other means such as small molecules.

Given that the Rad51 proteins are known to self-associate, the Rad51 protein sequence provides a template for the identification and genesis of peptides or factors that disrupt Rad51 function or activity. Accordingly, an additional embodiment of the present invention are peptides or polypeptides that correspond at least five contiguous amino acids of the mammalian Rad51 amino acid sequence (SEQ ID NO. 1), or the human Rad51 amino acid sequence (SEQ ID NO. 2) that retain the property of being capable of binding a mammalian Rad51 and/or inhibiting Rad51 function (as detected using a suitable biochemical, genetic, or cellular assay).

Additionally, the blocking of normal Rad51 function may induce programmed cell death. Thus, one aspect of the present invention are a novel class of therapeutic agents, factors, or compounds that have been engineered, or are otherwise capable of disrupting the essential processes that are mediated by, or associated with, normal Rad51 or Rad52 activity. Accordingly, it is contemplated that this novel class of therapeutics agents may be used to treat diseases including, but not limited to, autoimmune disorders and diseases, inflammation, cancer, graft rejection, and any of a variety of proliferative or hyperproliferative disorders.

Typical examples of therapeutic agents based on the above presently described molecules include, but are not limited to, defective (either engineered or naturally occurring) forms of the proteins that associate with the protein complexes, inhibitory fragments of the proteins, wild type and altered genes that code for proteins that disrupt mammalian Rad51 function, small organic molecules, antisense nucleic acid sequences, oligonucleotides that inhibit expression or activity via a triplex mechanism, peptides, aptameric oligonucleotides, and the like.

More particularly, examples of engineered proteins may include, but are not limited to, proteins that comprise inactivating mutations in conserved active sites (e.g., ATP binding motifs, DNA or protein binding domains, catalytic sites, etc.), fusion proteins that comprise at least one inhibitory domain, and the like.

The above agents may be obtained from a wide variety of sources. For example, standard methods of organic synthesis may be used to generate small organic molecules that mimic the desired regions of the target DNA repair proteins. In addition, combinatorial libraries comprising a vast number of compounds (organic, peptide, or nucleic acid, reviewed in Gallop et al. 1994, J. Med. Chem. 37(9):1233–1251; Gordon et al., 1994, J. Med. Chem. 37(10):1385–1401; and U.S. Pat. No. 5,424,186 all of which are herein incorporated by reference) may be screened for the ability to bind and inhibit the activity of proteins involved in DSB repair or any other potential mammalian Rad51 function.

In particular, inhibitory peptides should prove very useful. Such compounds may include, but are not limited to, peptides such as, for example, soluble peptides, including but not limited to members of random peptide libraries; (see, e.g., Lam et al., 1991, Nature 354:82–84; Houghten et al., 1991, Nature 354:84–86), and combinatorial chemistry-derived molecular library made of D- and/or L-configuration amino acids, phosphopeptides (including, but not limited to members of random or partially degenerate, directed phosphopeptide libraries; see, e.g., Songyang et al., 1993, Cell 72:767–778).

Given that they will serve as templates for the rational design of agents for disrupting DSB repair activity in the cell, it would be advantageous to purify each of the individual proteins that are directly or indirectly involved in DSB repair of any other potential mammalian Rad51 function. The various proteins involved in the DSB repair pathways may be purified using any of a number of variations of well established biochemical, and molecular biology techniques. Such techniques are well known to those of ordinary skill in the biochemical arts and have been extensively described in references such as Berger and Kimmel, *Guide to Molecular Cloning Techniques, Methods in Enzymology, Volume* 152, Academic Press, San Diego, Calif. (1987; *Molecular Cloning: A Laboratory Manual*, 2d ed., Sambrook, J., Fritsch, E. F., and Maniatis, T. (1989); Current Protocols in *Molecular Biology*, John Wiley & Sons, all Vols., 1989, and periodic updates thereof); *New Protein Techniques: Methods in Molecular Biology*, Walker, J. M., ed., Humana Press, Clifton, N.J., 1988; and *Protein Purification: Principles and Practice*, 3rd. Ed., Scopes, R. K., Springer-Verlag, New York, N.Y., 1987. In general, techniques including, but not limited to, ammonium sulfate precipitation; centrifugation, ion exchange, gel filtration, and reverse-phase chromatography (and the HPLC or FPLC forms thereof) may be used to purify the various proteins of the DSB repair complex.

Additionally, purified preparations of the presently described DNA repair proteins, associated proteins, or fragments thereof, may be used to generate antisera specific for a given agent. Accordingly, additional embodiments of the present invention include polyclonal and monoclonal antibodies that recognize epitopes of the presently described DNA repair complex proteins. The factors used to induce the antibodies of interest need not be biological active; however, the factors should induce immunological activity in the animal used to generate the antibodies.

Given that similar methodologies may be applied to the generation of antibodies to the various factors, for purposes of convenience, only the Rad51 factor antibodies will be discussed further.

Polypeptides for use in the induction of Rad51-specific antibodies may have an amino acid sequence consisting of at least three amino acids, and preferably at least 10 amino acids, that mimic a portion of the amino acid sequence of Rad51, and may contain the entire amino acid sequence of naturally occurring Rad51 or a Rad51-derivative.

Anti-Rad51 antibodies are expected to have a variety of medically useful applications, several of which are described generally below. More detailed and specific descriptions of various uses for anti-Rad51 antibodies are provided in the sections and subsections which follow. Briefly, anti-Rad51 antibodies may be used for the detection and quantification of Rad51 polypeptide expression in cultured cells, tissue samples, and in vivo. Such immunological detection of Rad51 may be used, for example, to identify, monitor, and assist in the prognosis of neoplasms that have been treated with factors that inhibit DSB repair. Additionally, monoclonal antibodies recognizing epitopes from different parts of the Rad51 structure may be used to detect and/or distinguish between native Rad51 and various subcomponent and/or mutant forms of the molecule. Additionally, anti-Rad51 monoclonal antibodies may be used to test preparations of agents or factors that mimic segments of Rad51, or are designed to impair protein association with Rad51, or to competitively inhibit DNA binding. In addition to the various diagnostic and therapeutic utilities of anti-Rad51 antibodies, a number of industrial and research applications will be obvious to those skilled in the art, including, for example, the use of anti-Rad51 antibodies as affinity reagents for the isolation of Rad51-associated polypeptides, and as immunological probes for elucidating the biosynthesis, metabolism and biological functions of Rad51. Rad51 antibodies may also be used to purify Rad51 or Rad51-associated factors by affinity chromatography.

Once purified, the proteins of interest may be partially sequenced, and these data may be used to design degenerate oligonucleotide probes for use in cloning the genes encoding the various proteins that are associated with DSB repair. Alternatively, any of a variety of public or private sequence data bases may be searched for nucleic acid or peptide sequences that share homology with genes and proteins associated with Rad51-mediated DSB repair. Once a similar sequence is identified, peptides may be produced and screened for inhibitory activity. Where a nucleic acid library is involved, one could synthesize a probe corresponding to the nucleic acid sequence of interest, and use the probe to clone a full-length version of the corresponding gene (if necessary). Accordingly, an additional embodiment of the presently claimed invention are nucleic acid sequences that are capable of hybridizing to sequences encoding the proteins that are associated with DSB repair under stringent conditions. For the purposes of the present invention, the term "stringent conditions" generally refers to hybridization conditions that (1) employ low ionic strength and high temperature for washing, for example, 0.015 M NaCl/0.0015 M sodium citrate/0.1% SDS at 50° C.; or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS. The above examples of hybridization conditions are merely provided for purposes of exemplification and not limitation. A more thorough treatise of the such routine molecular biology techniques may be found in Sambrook et al., Molecular Cloning, Cold Spring Harbor Laboratory Press, Cold Spring Harbor, N.Y., Vols. 1–3: (1989), and periodic updates thereof, herein incorporated by reference.

Once isolated, the genes encoding the proteins involved in DSB repair may be recombinantly expressed using standard vectors and hosts. Examples of vectors that may be used to express proteins of interest are provided in Sambrook et al., Molecular Cloning, Cold Spring Harbor Laboratory Press, Cold Spring Harbor, N.Y., Vols. 1–3: (1989). In particular, eucaryotic viruses may be used as vectors to transduce any of a wide variety of plant and animal cells to over express the desired proteins. Examples of such viruses include, but are not limited to, adenovirus, papilloma virus, herpes virus, adeno-associated virus, rabies virus, bacculo virus, retrovirus, plant viruses, and the like (See generally, Sambrook et al., *Molecular Cloning*, Cold Spring Harbor Laboratory Press, Cold Spring Harbor, N.Y., Vol. 3:16.1–16.89 (1989); U.S. Pat. No. 5,316,931, issued May 31, 1994, herein incorporated by reference).

Preferably, agents that disrupt DSB repair shall be substantially specific for blocking the desired repair pathways. For the purposes of the present invention, the term substantially specific shall mean that a given agent is capable of being dosaged to provide the desired effect while not causing undue cellular toxicity.

One of ordinary skill will appreciate that, from a medical practitioner's or patient's perspective, virtually any alleviation or prevention of an undesirable symptom (e.g., symptoms related to disease, sensitivity to environmental or factors, normal aging, and the like) would be desirable. Thus, for the purposes of this Application, the terms "treatment", "therapeutic use", or "medicinal use" used herein shall refer to any and all uses of compositions comprising the claimed agents which remedy a disease state or symptoms, or otherwise prevent, hinder, retard, or reverse the progression of disease or other undesirable symptoms in any way whatsoever.

When used in the therapeutic treatment of disease, an appropriate dosage of presently described agents, or derivatives thereof, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Before human studies of efficacy are undertaken, Phase I clinical studies in normal subjects help establish safe doses.

Additionally, the bioactive agents may be complexed with a variety of well established compounds or structures that, for instance, enhance the stability of the bioactive agent, or otherwise enhance its pharmacological properties (e.g., increase in vivo half-life, reduce toxicity, etc.).

Another aspect of the present invention includes formulations that provide for the sustained release of DSB repair antagonists. Examples of such sustained release formulations include composites of biocompatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279–292 (1992). Additional guidance in selecting and using polymers in pharmaceutical formulations can be found in the text by M. Chasin and R. Langer (eds.), "Biodegradable Polymers as Drug Delivery Systems," Vol. 45 of "Drugs and the Pharmaceutical Sciences," M. Dekker, New York, 1990. Liposomes may also be used to provide for the sustained release of DSB repair antagonists. Details concerning how to use and make liposomal formulations of drugs of interest can be found in, among other places, U.S. Pat. Nos. 4,944,948; 5,008,050; 4,921,706; 4,927,637; 4,452,747; 4,016,100; 4,311,712; 4,370,349; 4,372,949; 4,529,561; 5,009,956; 4,725,442; 4,737,323; 4,920,016. Sustained release formulations are of particular interest when it is desirable to provide a high local concentration of DSB repair antagonist, e.g., near a tumor, site of inflammation, etc.

Where diagnostic, therapeutic or medicinal use of the presently described agents, or derivatives thereof, is contemplated, the bioactive agents may be introduced in vivo by any of a number of established methods. For instance, the agent may be administered by inhalation; by subcutaneous (sub-q); intravenous (I.V.), intraperitoneal (I.P.), or intramuscular (I.M.) injection; or as a topically applied agent (transdermal patch, ointments, creams, salves, eye drops, and the like).

Additionally, an alternative means for employing the presently disclosed anti-proliferation agents includes the use of vectors to directly insert genes encoding the agents into target cells (e.g., gene therapy). For example, when the tumor cells express the genes encoding the desired sequences, DSB repair will be disrupted and the tumor cell will die. Alternatively, one could attack tumor cells using a strategy conceptually similar to that disclosed in U.S. Pat. No. 5,529,774 herein incorporated by reference. In brief, cells that produce transducing virus encoding sequence that disrupts DSB repair may be implanted at or near the tumor mass. As the producer cells continue to elaborate virus, the growing tumor cells are infected and effectively killed as they expressing the agent that blocks DSB repair. The above methodology has proven useful in the treatment of glioblastomas and other tumors of the brain by using retroviral vectors to selectively target actively replicating tumor cells. A similar methodology could be used to deliver antisense sequences that target (and thus inhibit) the expression of Rad51 or any of the proteins involved in the Rad51 or Rad52 pathways.

The mammalian Rad51- or Rad52-mediated repair pathways, and the associated proteins, are essential for cell proliferation or viability. These DNA repair pathways most likely function by repairing DSB via homologous recombination between sister chromatids during S/G$_2$ (recombinational repair); however, during G$_1$, the repair of DSB may also occur via nonhomologous recombination (nonhomologous end joining). The nonhomologous recombination pathway was once thought to be the major repair pathway in mammalian cells. Much of this belief stems from gene targeting data that demonstrated homologous recombination to be less frequent than random or illegitimate recombination (Bradley et al., 1992, Bio/Technology 10:534–39). Other data demonstrated that chromosomal DSB frequently were joined without homology or with only very short stretches of homology (Rouet and Jasin, 1994, Mol. Cell. Biol. 14:8096–8105). DNA-dependent protein kinase (DNA-PK) is critical for nonhomologous but not homologous repair of DSB (Liang et al., 1996, Proc. Natl. Acad. Sci. USA 93:8929–33). A biphasic response to ionizing radiation was observed in DNA-PK-deficient cell lines with resistance in late S phase suggesting that DNA-PK functions in G$_1$ and another repair pathway functions in S phase (Jeggo, 1990, Mutation Research 239:1–16). DNA-PK is composed of a catalytic subunit called DNA-PK$_{cs}$ and a DNA end-binding subunit called Ku which is a heterodimer of Ku70 and Ku86 (Park et al., 1996, J. Biol. Chem. 1996:18996–19000, for review, see Roth et al., 1995; Shen et al., 1996. Analysis of DNA-PK activity has come from said (severe combined immunodeficient) mice which are deficient in DNA-PK$_{cs}$ (Kirchgessner et al., 1995, Science 267:1178–82), and Ku86-deficient mice (Nussenzweig et al., 1996, Nature 382:551–55; Zhu et al., 1996, Cell 86:379–89). Both said and Ku86-deficient mice are immune deficient due to a defect in repair of DSB generated during V(D)J recombination. Unfortunately, it is impossible to analyze V(D)J recombination in rad51-mutant mice or cells; however, it is unlikely that MmRad51 plays a role in this process since MmRad51 localizes to the nucleus in late G$_1$ through G$_2$ (Yamamoto et al., 1996, 251:1–12), and V(D)J recombination occurs in G$_0$/G$_1$ (Schlissel et al., 1993, Genes & Dev. 7:2520–32). In general, said and Ku86-deficient cells do have similarities to MmRad51-deficient cells. All are hypersensitive to ionizing radiation, and Ku86-deficient cells were prematurely senescent in tissue culture, indicating a similar function. However, since scid and Ku86-deficient mice and cells were viable and MmRad51-deficient cells were not, the consequences of removing the putative homologous recombination pathway to repair DSB appears to be more vital than the removal of the nonhomologous pathway.

The presently described DSB repair antagonists are particularly deemed useful for the treatment of cancer. Cancers that may be treated by the methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastom, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia)! ovaries (ovarian carcinoma [serous cystadenocarcinoma, mucinous cystadenocarcinoma, endometrioid tumors, celioblastoma, clear cell carcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematoloqic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles, dysplastic nevi, lipoma, angioma, dermatofibroma, keloids, psoriasis; and Adrenal glands: neuroblastoma.

In addition to cancer, the presently disclosed compounds are effective against any of a wide variety of hyperproliferative disorders including, but not limited to: autoimmune disease, arthritis, inflammatory bowel disease, proliferation induced after medical procedures, including, but not limited to, surgery, angioplasty, and the like.

The anti-cancer application of agents that functionally disrupt mammalian Rad51, Rad52 or any member in the DSB repair pathway, requires that DSB repair remains equally critical in cancer cells. Cancer cells lack many of the normal cell cycle regulatory mechanisms that are critical to controlling proliferation, and inducing programmed cell death, and it remains possible that the absence of these mechanisms renders Rad51 and/or Rad52 function nonessential. The protein p53 is central to regulation of the cell cycle, and stimulation of cell death in response to DNA damage including DNA damaged by ionizing radiation (reviewed by Ko and Prives, 1996, Genes & Develop. 10:1054–72). p53 is the most commonly mutated gene in cancer cells (Donehower et al., 1992, Nature 356:215–21; Vogelstein, 1990, Nature 348:681–682) and mutations in p53 are known to increase cell proliferation and promote chromosomal instability (Harvey et al., 1993, Oncogene 8:2457–67).

The early lethal phenotype in rad51$^{M1}$ mutant embryos and cells may be stimulated by a cell cycle response to unrepaired DNA damage. DNA damage was shown to inhibit progression through the cell cycle, demonstrating a relationship between DNA lesions and cell cycle proteins (Carr and Hoekstra, 1995, Trends in Cell Biology 5:32–40). In mitotically dividing budding yeast cells, a single DSB in a dispensable plasmid was sufficient to induce cell death, partly under the control of Rad9 (Bennett et al., 1993, Proc. Natl. Acad. Sci. USA 90:5613–17; Schiestl et al., 1989, Mol. Cell. Biol. 9:1882–9654, Weinert and Hartwell, 1988, Science 241:317–22). In mammalian cells, the tumor suppressor gene, p53, responded to DNA damage induced by T-radiation by delaying the cell cycle, or inducing programmed cell death (Kastan et al., 1991, Cancer Research 51:6304–11; Kuerbitz et al., 1992, Proc. Natl. Acad. Sci. USA 89:7491–95). These responses may be critical the tumor suppressor function of p53 (Baker et al., 1990, Science 249:912–15; Lowe et al., 1994, Science 266:807–10, Symonds et al., 1994, Cell 78:703–11). Induction of p53 after exposure to ionizing radiation and restriction endonuclease suggest that the formation of DSB may initiate a p53 response (Lu and Lane, 1993, Cell 75:765–78).

p53 was at least partly responsible for regulating the rad51$^{M1}$ phenotype because development was extended from the early egg cylinder stage to the head fold stage in a p53-mutant background. However, the double-mutant embryos died from either accumulation of DNA damage resulting in metabolic incompetence and mitotic failure, or p53-independent regulation. Murine embryonic fibroblasts, generated from double-mutant embryos, failed to proliferate and were completely senescent in tissue culture; thus, demonstrating that MmRad51 function was critical in cells that exhibit chromosomal instability and accelerated proliferation. It is therefore likely that disruption of MmRad51 or any other protein in its pathway or disruption of any protein-protein interaction important in the DSB repair pathway results in reduced proliferation or decreased cell viability. This feature remains true even in cells with reduced capacity to regulate the cell cycle.

The present invention is further illustrated by the following examples, which are not intended to be limiting in any way whatsoever.

5.0. EXAMPLES
5.1. Cloninc of the Mouse MmRAD51 cDNA

The MmRAD51 cDNA sequence was cloned and used to generate an expression vector. The 5' end of cDNA was amplified by RT-PCR from mouse testis RNA and was then used as a probe to screen a mouse brain cDNA library. One clone was identified and sequenced. The coding sequence was identical to MmRAD51 disclosed in published reports (Morita et al., 1993; Shinohara et al., 1993); however, the clone contained about 300 additional base pairs of 5' noncoding sequence and about 400 extra base pairs of 3' noncoding sequence (FIG. 1).

5.2. The Use of a Yeast Two-Hybrid Screen to Isolate Proteins That Associate with MmRad51

ScRad51 was shown to self-associate as well as associate with other proteins such as ScRad52 and ScRad55 (Donovan et al., 1994; Hays et al., 1995; Johnson and Symington, 1995; Milne and Weaver, 1993; Shinohara et al., 1992). Kluyveromyeces lactis RAD51 and RAD52 did not rescue a rad51Δ rad52Δ strain of S. cerevisiae and over expression of ScRAD51 suppressed rad55 and rad57 mutant yeast which indicates interacting proteins are necessary (Donovan et al., 1994; Hays et al., 1995). Also, Dmc1 and ScRad51 colocalized to the synaptonemal complex which suggested that they act together during meiotic recombination (Bishop, 1994).

The modified yeast two-hybrid system was used to isolate proteins that associate with mammalian Rad51 which is a genetic screen for determining protein-protein interactions (Harper et al., 1993). One of the proteins is a hybrid of the GAL4 DNA-binding domain fused to MmRad51 (the "bait"). The other is a hybrid of the GAL4 transactivating domain fused to an embryonic or a T cell cDNA library (the "prey"). The bait and prey were co-expressed in HF7c yeast that contained two reporters, HIS3 and lacZ fused to the GAL4 promoter and grown in media lacking histidine and containing 25 mM 3-AT (an antimetabolite; 3-amino-1,2,4-triazole). Functional GAL4 was created when the DNA binding domain and the transactivation domain were juxtaposed, ideally by a MmRad51-protein interaction. Such an interaction induced the HIS3 and lacZ genes allowing a positive colony to survive in medium lacking histidine and to turn blue in X-Gal (5-bromo-4-chloro-3-indolyl-β-D-galactosidase).

Seven specific clones were isolated from this screen. A 13.5 day embryonic cDNA library (500 μg) was transfected into 5×10$^6$ cells and plated onto forty 15 cm plates. A T cell cDNA library (400 μg) was transfected into 4×10$^6$ cells and plated onto twenty 15 cm plates. A total of 80 His$^+$ colonies grew in about 3 days. Of these, 40 turned blue after about 5 to 30 minutes of exposure to X-gal. These colonies were tested for specificity by transfecting HF7c cells without bait or with a nonspecific bait (E12). Nonspecific associations were observed in 20 clones. The inserts in the other clones were sequenced and 13 were out of frame and seven were in frame. The sequences for the remaining seven clones were screened in the GCG data base. Homologues were found for four clones and three clones were novel (Table 1). The protein produced by clone 1 was 100% homologous to MmRad51 which showed that the screen was successful because RecA and ScRad51 are both known to self-associate. The protein produced from clone 2 was 100% homologous to a metal response element binding protein, M96 (Inouye et al., 1994, DNA and Cell Biol. 13(7): 31–742). The function of M96 is unknown. The protein produced from clone 3 was 48% homologous to human XP-G (ERCC-5) and 45% homologous to chicken Histone H1. A mutation in XP-G is responsible for the genetic disorder xeroderma pigmentosum (Cleaver, 1994; Cleaver and Kraemer, 1995, In The metabolic basis of inherited disease, p. 4393–4419, 7th ed. McGraw-Hill, New York.). XP-G is a homologue of the S. cerevisiae excision repair protein, ScRad2 which is a ssDNA endonuclease. It is possible that MmRad51 repairs single-strand breaks as well as double-strand breaks and that single-strand breaks can initiate recombination. Histone H1 is a component of the nucleosome and comprises a group of related proteins that vary in tissues and are poorly conserved across species. The length of DNA may be affected by Histone H1 binding to the linker region and joining adjacent nucleosomes. The protein produced from clone 4 was 100% homologous to the human breast cancer gene, BRCA2 (Tavtigian et al., 1996, Nat. Gen. 12:333 –337; Wooster et al., 1995, Nature 378:789–792). The function of Brca2 is unknown; however, like p53, it is a tumor suppressor gene and may therefore regulate the cell cycle in response to DNA damage. Thus, the observed association with a DNA repair gene, MmRad51, is consistent with such an activity.

TABLE 1

Clones isolated from the yeast two-hybrid screen

| Clone | Homology | Library |
|---|---|---|
| 1 | 100% to MmRad51 | T cell |
| 2 | 100% to M96 | embryo |
| 3 | 45% to Histone H1, 48% to to XP-G | embryo |
| 4 | 100% to Brca2 | T cell |
| 5 | novel | T cell |
| 6 | novel | embryo |
| 7 | novel | embryo |

Clones isolated from a yeast two-hybrid screen with MmRad51 as the "bait" and an embryonic or T cell cDNA library as the "prey". The inserts obtained from the prey were sequenced and compared to sequences in the GCG data base. The measured extent protein homology is listed. All clones strongly associated with MmRad51 in the N-terminal region (amino acids 1–43). Colonies grew with in three days in 3-AT, and cells generally stained blue after about 5 minutes of X-gal exposure.

5.3. Deletion Analysis of MmRad51 to Isolate the Protein Association Region

A deletion analysis was performed to isolate the MmRad51 self-association domain. Full length MmRAD51 was used as the bait and deletions of MmRAD51 were the prey (FIG. 2). The "prey" MmRad51 deletions were individually co-transfected with the bait into HF7c cells. The relative levels of β-galactosidase activity were measured for the MmRad51 deletion proteins as compared to full length MmRad51 which was considered to have 100% activity. Expression of the C-terminal region, TR43-339 and TR131-339 did not result in blue yeast cells after 10 hours, and the relative β-galactosidase activity was about 1%, or the same as for the nonspecific bait, E12. However, expression of the N-terminal region, TR1-43, stained yeast cells blue in less than 5 minutes and the relative β-galactosidase activity was 43%. Interestingly, a sequence containing more of the N-terminal region of the protein, TR1-93, caused the yeast cells to stain blue after about 30 minutes of X-gal exposure, and reduced the relative β-galactosidase activity to about 4%. In similar experiments, TR1-131 and TR1-175 respectively displayed 11% and 9% of the β-galactosidase activity of the positive control. Nevertheless, these data indicated that the N-terminal region was responsible for MmRad51 self-association. It also appeared that amino acids 43–93 inhibited self-association and that this inhibition was relieved by adding more of the C-terminal region of the protein. These data indicated that MmRad51 was functionally conserved with ScRad51 since the self-association domain was also in the N-terminal region for both proteins even though these regions did not display conserved amino acid sequences.

The other six proteins listed in Table 1 were tested to determine if they interacted with the N-terminal region of MmRad51. All six strongly interacted with TR1-43; thus, the most N-terminal 43 amino acids were responsible for all the MmRad51 protein-protein interactions observed. Given the high level of homology shared between the human and murine Rad51 proteins (in the important N-terminal self-association region, the proteins only differ at amino acid positions 10 and 46 where the human sequence respectively contains an asparagine in lieu of the serine, and a phenylalanine in place of the tyrosine encoded by the mouse protein—both relatively conservative replacements), the presently described results should reflect the results expected from similar studies using the human Rad51 protein.

6.4. Transfection of Mouse Embryonic Stem Cells with Altered Alleles of Mammalian rad51

Both MmRad51 and ScRad51 self-associate using their respective N-terminal regions. This observation supports the hypothesis for that these proteins remain functionally conserved. Functional conservation was further tested in the RecA core homology domain. In ScRad51, the RecA core homology region was shown to be essential for the repair of DSB. The gene rad51K-A191 was altered in the first ATP-binding motif, and a conserved Lysine was changed to an Alanine. The expression of rad51K-A191 in wild-type yeast cells dominantly impaired the repair of DNA damage and generated a rad51 null phenotype. Nonproductive protein-protein interactions were probably responsible for the dominant negative phenotype because rad51K-A191 was shown to associate with wild-type ScRad51 and ScRad52. If the MmRad51 structural domains were similar to ScRad51, then disruption of the conserved Lysine in the first ATP-binding motif should result in a null phenotype because of the nonfunctional associations with wild-type MmRad51 or other proteins in this pathway such as mouse Rad52 or Brca2. A null rad51 mutation resulted in a severe cell proliferation defect that prevented propagation of mutant mouse cells in tissue culture. Therefore, cells that expressed a dominant negative rad51 allele should not be recovered due to this proliferation defect.

Altered alleles of mammalian rad51 that were engineered to be dominate negative were expressed in mouse embryonic stem cells. Due to the severity of the null phenotype, these experiments were designed to measure the absence of transfected cells by statistically relevant numbers. The first experiment measured the transfection efficiencies of vectors that expressed altered mammalian rad51 as compared to a vector that expressed wild-type mammalian RAD51, or vector alone. The altered transgenes, rad51TR1-131 and rad51K-A134, contained a functional protein binding region and a nonfunctional RecA homology region. For rad51TR1-131, a C-terminal truncation was made in the first ATP-binding domain (FIG. 1). For rad51K-A134, the conserved Lysine in the first ATP-binding motif was changed to an Alanine (for review, see Donovan and Weaver, 1994). rad51K-A134 more strongly associated with full length MmRad51 than rad51TR1-131 as measured using the yeast two-hybrid system with about 90% relative β-galactosidase activity (FIG. 1). The altered and wild-type transgenes were cloned into a CMV expression vector with a neomycin phosphotransferase (neo) cassette (pcDNA3 from invitrogen). Transfected embryonic stem (ES) cells were selected in G418 and colonies were counted 9 days later. The altered transgenes generated 20–30% fewer G418$^r$ colonies as compared to colonies resulting after transfection with wild-type MmRAD51 or vector alone in three experiments. Variations of 20–30% in transfection frequencies are commonly observed and are consequently not determinative in and of themselves. However, this minimal reduction could also indicate that the toxic product of the altered transgenes was produced in sufficient quantities to stop cell proliferation. However, if the transgene product was truly toxic, then why did 70–80% of the cells survive in selection media? The transgene may be silent while neo gene is expressed. The transgene may be disrupted upon integration into the chromosome or by chromosomal positional effects. In addition, strong expression of the transgene may be required to observe a phenotype while only weak expression of neo may be required for positive selection. Another experiment was needed to circumvent these possible problems.

6.5. Targeting the Expression Vectors to the HPRT Locus

Another experiment was developed to compare the targeting frequencies of vectors that expressed altered mammalian rad51 with vectors that expressed wild-type mammalian RAD51 or MC1tk (Herpes Simplex Virus type 1 *thymidine kinase*). The transgenes were targeted to the hypoxanthine phosphoribosyltransferase locus, HPRT (Melton et al., 1984, Proc. Natl. Acad. Sci. USA 81:2147–2151). Targeting the transgenes to HPRT would decrease the likelihood of disruption upon integration and Southern analysis could also be used to verify the integrity of the integration event (FIG. 3). The transgenes would also be located to a favorable environment for expression since HPRT is a house keeping gene, and thus all of the transgenes would be affected to the same degree by chromatin positional effects. The transgenes were cloned into the bacterial plasmid of an insertion vector that targeted HPRT (IVH). There were 6.9 kb of HPRT sequences that contained a neo cassette in exon 3. Therefore, upon linearization using a unique site in the homology region (an engineered NotI site), both insertion and replacement events could be recovered.

The targeting vectors were linearized in the HPRT homology region and transfected into ES cells. Transfected cells were selected for by growth in medium containing G418, and targeted cells were selected in medium containing G418+6-thioguanine (TG). G418 resistant (G418$^r$) colonies were counted to measure the transfection efficiency and TG$^r$+G418$^r$ colonies were counted to measure the targeting frequency.

TABLE 2

Targeting frequencies

|  | Exp. | No. of Exps. | total G418$^r$ | total TG$^r$ | TG$^r$ + G418$^r$ | target frequency relative to IVH-tk |
|---|---|---|---|---|---|---|
| IVH-tk | A | 2 | 4088 | 338 | 1/12 | NA |
| IVH-51TA |  | 1 | 636 | 34 | 1/19 | −37% |
| IVH-51KA |  | 2 | 2792 | 106 | 1/26 | −54% |
| IVH-tk | B | 2 | 1200 | 124 | 1/10 | NA |
| IVH-51TA |  | 2 | 472 | 22 | 1/21 | −52% |
| IVH-51KA |  | 2 | 1504 | 62 | 1/24 | −58% |
| IVH-tk | C | 2 | 6016 | 264 | 1/23 | NA |
| IVH-51WT |  | 2 | 4840 | 192 | 1/26 | −12% |
| IVH-51TA |  | 2 | 2584 | 70 | 1/37 | −38% |
| IVH-51KA |  | 2 | 3664 | 48 | 1/76 | −70% |
| IVH-tk | D | 2 | 6744 | 414 | 1/16 | NA |
| IVH-51KA |  | 2 | 4848 | 136 | 1/37 | −57% |
| IVH-tk | E | 2 | 2624 | 186 | 1/14 | NA |
| IVH-51WT |  | 2 | 1456 | 84 | 1/17 | −18% |
| IVH-51TA |  | 2 | 2208 | 96 | 1/23 | −39% |
| IVH-51KA |  | 2 | 1376 | 52 | 1/26 | −46% |
| IVH-tk | F | 2 | 1664 | 156 | 1/11 | NA |
| IVH-51WT |  | 2 | 752 | 60 | 1/12 | −8% |
| IVH-51TA |  | 2 | 760 | 34 | 1/22 | −50% |
| IVH-51KA |  | 2 | 544 | 30 | 1/18 | −39% |

Electroporation: 10 μg of NotI cut DNA/10$^7$ cells/ml PBS, 575 V/cm and 500 μF. Each experiment (exps. A–F) shows results from electroporations that were done on the same day with a common batch of ES cells under identical conditions to eliminate variability. NA, not applicable.

The targeting frequencies of vectors that contained altered rad51 alleles were compared to control vectors (Table 2). Vectors that contained altered rad51 alleles were IVH-51TR1-131 (contains rad51TR1-131) and IVH-51KA (contains rad51K-A134). Control vectors were IVH-51WT (contains wild-type MmRAD51), and IVH-tk (contains MC1tk). The relative targeting frequencies (TG$^r$+G418$^r$/G418$^r$ colonies) were determined using IVH-tk efficiency as 100%. The relative targeting frequencies were reduced by 13+/−3.6% for IVH-51WT (average of three experiments), 43+/−6.4% for IVH-51TR1-131 (average of 5 experiments) and 54+/−7.6% for IVH-51KA (average of six experiments).

Southern analysis was performed on TG$^r$+G418$^r$ clones to verify targeting and to identify the different targeting patterns (FIG. 3). Several types of recombination patterns were possible. A vector insertion event would integrate the entire vector to form a duplication of HPRT homology (Hasty et al., 1992, Molec. and Cell. Biol. 12:2464–2474). The vector may integrate on the 5' long arm or the 3' short arm (rarely observed). These integration patterns were combined since both integrate the transgene in between the duplication. A gene replacement event would introduce the neo but not the transgene and thus, provided a control. Modified events, that were not predicted by either pattern could also occur, and an intact transgene may or may not be introduced.

Comparison of the targeting patterns for the four vectors indicated that the transgene product was toxic for both rad51TR1-131 and rad51K-A134. The relative percentage of clones targeted with IVH-51TR1-131 and IVH-51KA that contained the transgene (vector insertion) decreased, and the relative percentage of targeted clones that did not contain the transgene (gene replacement) increased relative to controls. For both IVH-tk and IVH-51WT, targeting usually occurred by vector insertion (75% and 80%, respectively), rarely by gene replacement (14% and 17%, respectively), or more rarely by a modified event (6% and 8%, respectively). However, for IVH-51TR1-131 and IVH-51KA the relative frequency of targeted events that occurred by vector insertion decreased (68% and 45%, respectively), and gene replacement events increased (27% and 41%, respectively). The relative frequency of modified events also increased for clones targeted with IVH-51KA (14%). Therefore, the altered transgenes rarely integrated into the target locus as compared to the controls.

6.6. A High Percentage of Transfected Clones did not Express the Transpene

A statistically significant reduction in targeting frequency was observed using vectors that contained the altered rad51 alleles as compared to the wild-type allele or MC1tk. In addition, altered transgenes were introduced into HPRT for a lower percentage of the targeted clones as compared to the controls. However, targeted clones were generated that appeared to incorporate the altered transgenes intact. There are several possibilities for survival: 1) A small mutation may have been generated in the transgene; 2) The chromatin structure of the transgene may have been altered during the targeting event to silence the transgene (or vice-versa); 3) Position effect variegation may inhibit transcription of the transgene, but not neo.

Expression of MC1tk was tested in clones targeted with IVH-tk to determine the fraction of clones that do not express the transgene. Sixty-two TG$^r$+G418$^r$ clones were grown in replica plates, one without FIAU and one with FIAU, to distinguish clones that lost or maintained HSV-1 thymidine kinase activity. A large percentage of clones (42%) survived in FIAU demonstrating that the IVH-51TR1-131 and IVH-51KA targeting frequencies were reduced to background levels. Therefore, all of the cells targeted with either IVH-51TR1-131 and IVH-51KA that express the transgene were probably not recovered.

6.7. Application of Molecules that Disrupt Mammalian Rad51 and/or Rad52 Function for Cancer Therapeutics The rad51$^{M1}$ mutation reduces proliferation and promotes cellular senescence, even in a p53 mutant background. In addition, rad51 dominant negative alleles also display this phenotype by presumably forming nonproductive protein associations with Rad51 and other proteins like Rad52, M96 and Brca2. Therefore, it is likely that the disruption of mammalian Rad51, mammalian Rad52 (or any protein in the DSB repair pathway mediated by these proteins) will reduce cell proliferation or induce cell death, and thus be suitable as a cancer therapeutic. In addition, the disruption of any protein-protein association important for mammalian Rad51 function or mammalian Rad52 function will also reduce cell proliferation or induce cell death, and thus be suitable as a cancer therapeutic.

Additionally, dominate negative alleles of rad51 may be used to express cancer therapeutics that reduce cell proliferation or induce cell death. An expression vector that codes for a dominate negative rad51 allele may be introduced into cancer cells, or an mRNA that codes for a dominate negative rad51 allele may be introduced into cancer cells, or a dominate negative Rad51 protein may be introduced into cancer cells. Several examples of such dominate negative rad51 alleles are presently disclosed. Of these alleles, the protein encoded by rad51K-A131 appears to have the strongest self-association, and proved toxic to proliferating cells. In fact, any rad51 allele that rendered the RecA homology region nonfunctional but preserved the N-terminal protein association region should reduce cell proliferation or induce cell death and could thus be used as a cancer therapeutic.

In addition to subtle alterations in the RecA core homology region of mammalian Rad51, C-terminal truncations in mammalian rad51 may also be used to reduce cell proliferation and/or induce cell death. rad51TR1-131 demonstrated a toxic effect on cells even though it had a relatively weak interaction with MmRad51 which suggested that the phenotype might be caused by nonfunctional self-associations, or nonfunctional associations with other proteins such as Rad52, M96 and Brca2. rad51TR1-43 had a strong interaction with MmRad51 and may be more effective as a cancer therapeutic than rad51TR1-131. In fact, any C-terminal truncation that preserves the protein interacting region of Rad51 may be used as a dominate negative allele for cancer therapy. Additionally, fusion of the N terminal domain of mammalian Rad51 to the 16 or 60 amino acids of the 3rd helix of the antennapedia protein may promote entry into the nucleus (Derossi et al., 1994, J. Bio. Chem. 269:10444–10450).

Mammalian Rad51 interacts with other proteins besides itself, and disruption of these interactions could be used to reduce cell proliferation or induce cell death. Other proteins interacting with mammalian Rad51 include but are not limited to mammalian Rad52, Brca2 and M96.

The identification of other interacting proteins will further elucidate the pathway and present greater opportunities to disrupt this pathway for the purpose of hindering cell proliferation. Since mammalian Rad52 associates with mammalian Rad51 and other proteins (Park et al., 1996; Shen et al., 1996), dominant alleles of mammalian Rad52 may also hinder cell proliferation or induce cell death. Such alleles could also be used for cancer therapeutics. In fact, dominant alleles of any protein that associates with mammalian Rad51, Rad52 or any other protein in these pathways, may be expected to hinder cell proliferation or induce cell death. Thus, all of the above molecules collectively define a new class of therapeutic agents for the treatment of proliferative disorders, viral infection (especially HIV infection), and cancer.

EQUIVALENTS

The foregoing specification is considered to be sufficient to enable one skilled in the art to broadly practice the invention. Indeed, various modifications of the above-described makes for carrying out the invention which are obvious to those skilled in the field of microbiology, biochemistry, organic chemistry, medicine or related fields are intended to be within the scope of the following claims. All patents, patents applications, and publications cited are herein incorporated by reference.

What is claimed is:

1. A method of screening for compounds that disrupt mammalian double stranded break repair, comprising:
    a) contacting a mammalian cell with a compound to be screened;
    b) assaying for microsatellite formation in said cell;
    c) assaying for chromosome loss in said cell;
    d) assaying said compound for the disruption of strand exchange in an in vitro assay; and
    e) correlating assay results from steps b, c and d to identify a compound that disrupts mammalian double stranded break repair.

2. A method according to claim 1 wherein said compound is a molecule produced by cells.

3. A method according to claim 1 wherein said compound was chemically synthesized.

4. A method of screening for compounds that disrupt the function of mammalian Rad51, comprising:
    a) in a yeast two-hybrid system wherein mammalian Rad51 is one component, identifying a protein that interacts with mammalian Rad51;
    b) contacting said system with a compound to be screened; and c) correlating assay results from step b to identify a compound that disrupts the function of mammalian Rad51.

5. A method according to claim 4 wherein said compound is a molecule produced by cells.

6. A method according to claim 4 wherein said compound was chemically synthesized.

7. A method of screening for compounds that disrupt the function of mammalian Rad52, comprising:
  a) in a yeast two-hybrid system wherein mammalian Rad51 is one component identifying a protein that interacts with mammalian Rad51;
  b) contacting said system with a compound to be screened; and
  c) correlating assay results from step b to identify a compound that disrupts the function of mammalian Rad51;
    whereby disruption of the function of mammalian Rad51 is correlated with the disruption of mammalian Rad52.

8. A method according to claim 7 wherein said compound is a molecule produced by cells.

9. A method according to claim 7 wherein said compound was chemically synthesized.

10. A method of screening for compounds that disrupt the function of mammalian Rad51, comprising:
  a) in a biochemical binding assay system wherein Rad51 is one component, identifying a compound that is associated with mammalian Rad51;
  b) contacting said system with a compound to be screened; and
  c) correlating assay results from step b to identify a compound that disrupts the function of mammalian Rad51.

11. A method according to claim 10 wherein said compound is a molecule produced by cells.

12. A method according to claim 10 wherein said compound was chemically synthesized.

13. A method of screening for compounds that disrupt the function of mammalian Rad52, comprising:
  a) in a biochemical binding assay system wherein Rad51 is one component, identifying a compound that is associated with mammalian Rad51;
  b) contacting said system with a compound to be screened; and
  c) correlating assay results from step b to identify a compound that disrupts the function of mammalian Rad51;
    whereby disruption of the function of mammalian Rad51 is correlated with the disruption of mammalian Rad52.

14. A method according to claim 13 wherein said compound is a molecule produced by cells.

15. A method according to claim 13 wherein said compound was chemically synthesized.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 339 amino acids
      (B) TYPE: amino acid
      (C) STRANDEDNESS: Not Relevant
      (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:1:

Met Ala Met Gln Met Gln Leu Glu Ala Ser Ala Asp Thr Ser Val Glu
1           5                10               15

Glu Glu Ser Phe Gly Pro Gln Pro Ile Ser Arg Leu Glu Gln Cys Gly
         20                25               30

-continued

```
Ile Asn Ala Asn Asp Val Lys Lys Leu Glu Glu Ala Gly Tyr His Thr
         35                  40                  45
Val Glu Ala Val Ala Tyr Ala Pro Lys Lys Glu Leu Ile Asn Ile Lys
 50                  55                  60
Gly Ile Ser Glu Ala Lys Ala Asp Lys Ile Leu Thr Glu Ala Ala Lys
 65                  70                  75                  80
Leu Val Pro Met Gly Phe Thr Thr Ala Thr Glu Phe His Gln Arg Arg
                 85                  90                  95
Ser Glu Ile Ile Gln Ile Thr Thr Gly Ser Lys Glu Leu Asp Lys Leu
                100                 105                 110
Leu Gln Gly Gly Ile Glu Thr Gly Ser Ile Thr Glu Met Phe Gly Glu
                115                 120                 125
Phe Arg Thr Gly Lys Thr Gln Ile Cys His Thr Leu Ala Val Thr Cys
130                 135                 140
Gln Leu Pro Ile Asp Arg Gly Gly Gly Glu Gly Lys Ala Met Tyr Ile
145                 150                 155                 160
Asp Thr Glu Gly Thr Phe Arg Pro Glu Arg Leu Leu Ala Val Ala Glu
                165                 170                 175
Arg Tyr Gly Leu Ser Gly Ser Asp Val Leu Asp Asn Val Ala Tyr Ala
                180                 185                 190
Arg Gly Phe Asn Thr Asp His Gln Thr Gln Leu Leu Tyr Gln Ala Ser
                195                 200                 205
Ala Met Met Val Glu Ser Arg Tyr Ala Leu Leu Ile Val Asp Ser Ala
                210                 215                 220
Thr Ala Leu Tyr Arg Thr Asp Tyr Ser Gly Arg Gly Glu Leu Ser Ala
225                 230                 235                 240
Arg Gln Met His Leu Ala Arg Phe Leu Arg Met Leu Leu Arg Leu Ala
                245                 250                 255
Asp Glu Phe Gly Val Ala Val Val Ile Thr Asn Gln Val Val Ala Gln
                260                 265                 270
Val Asp Gly Ala Ala Met Phe Ala Ala Asp Pro Lys Lys Pro Ile Gly
                275                 280                 285
Gly Asn Ile Ile Ala His Ala Ser Thr Thr Arg Leu Tyr Leu Arg Lys
                290                 295                 300
Gly Arg Gly Glu Thr Arg Ile Cys Lys Ile Tyr Asp Ser Pro Cys Leu
305                 310                 315                 320
Pro Glu Ala Glu Ala Met Phe Ala Ile Asn Ala Asp Gly Val Gly Asp
                325                 330                 335
Ala Lys Asp
```

(2) INFORMATION FOR SEQ ID NO:2:

(i) SEQUENCE CHARACTERISTICS:
        (A) LENGTH: 339 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:2:

```
Met Ala Met Gln Met Gln Leu Glu Ala Asn Ala Asp Thr Ser Val Glu
 1               5                  10                  15
```

-continued

```
Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
            35                  40                  45

Val Glu Ala Val Ala Tyr Ala Pro Lys Lys Glu Leu Ile Asn Ile Lys
            50                  55                  60

Gly Ile Ser Glu Ala Lys Ala Asp Lys Ile Leu Ala Glu Ala Ala Lys
 65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
            100                 105                 110

Leu Gln Gly Gly Ile Glu Thr Gly Ser Ile Thr Glu Met Phe Gly Glu
            115                 120                 125

Phe Arg Thr Gly Lys Thr Gln Ile Cys His Thr Leu Ala Val Thr Cys
            130                 135                 140

Gln Leu Pro Ile Asp Arg Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
                180                 185                 190

Arg Ala Phe Asn Thr Asp His Gln Thr Gln Leu Leu Tyr Gln Ala Ser
            195                 200                 205

Ala Met Met Val Glu Ser Arg Tyr Ala Leu Leu Ile Val Asp Ser Ala
            210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Leu Arg Leu Ala
                245                 250                 255

Asp Glu Phe Gly Val Ala Val Val Ile Thr Asn Gln Val Val Ala Gln
                260                 265                 270

Val Asp Gly Ala Ala Met Phe Ala Ala Asp Pro Lys Lys Pro Ile Gly
            275                 280                 285

Gly Asn Ile Ile Ala His Ala Ser Thr Thr Arg Leu Tyr Leu Arg Lys
            290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp
```